(12) United States Patent
Baxter et al.

(10) Patent No.: US 10,874,501 B2
(45) Date of Patent: Dec. 29, 2020

(54) LOW PROFILE STENT GRAFT HAVING A CHECK VALVE

(71) Applicant: Cook Medical Technologies LLC, Bloomington, IN (US)

(72) Inventors: Charlie L. Baxter, West Lafayette, IN (US); Jarin A. Kratzberg, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/831,598

(22) Filed: Dec. 5, 2017

(65) Prior Publication Data

US 2018/0185132 A1 Jul. 5, 2018

Related U.S. Application Data

(60) Provisional application No. 62/439,586, filed on Dec. 28, 2016.

(51) Int. Cl.
*A61F 2/07* (2013.01)
*A61F 2/06* (2013.01)

(52) U.S. Cl.
CPC .................. *A61F 2/06* (2013.01); *A61F 2/07* (2013.01); *A61F 2002/065* (2013.01);
(Continued)

(58) Field of Classification Search
CPC .................. A61F 2/07; A61F 2002/075; A61F 2002/077; A61F 2/856; A61F 2/954; A61F 2002/065
See application file for complete search history.

(56) References Cited

U.S. PATENT DOCUMENTS 6,652,567 B1 11/2003 Deaton
6,746,489 B2 6/2004 Dua et al.
(Continued)

FOREIGN PATENT DOCUMENTS

EP 2491892 A1 8/2012
FR 2834199 A1 7/2003

OTHER PUBLICATIONS

Chuter et al., "An endovascular system for thoracoabdominal aortic aneurysm repair", Journal of Endovascular Therapy, 2001, vol. 8, pp. 25-33.
(Continued)

*Primary Examiner* — Suba Ganesan
(74) *Attorney, Agent, or Firm* — Brinks Gilson & Lione

(57) ABSTRACT

An endoluminal prosthesis is provided including an tubular graft having a proximal end, a distal end, and a main lumen disposed therein, the tubular graft comprising a first biocompatible material; a plurality of stents disposed about a surface of the tubular graft and arranged in longitudinally spaced rows; at least one aperture disposed through a sidewall of the tubular graft, the at least one aperture positioned between two longitudinally spaced rows of stents; a valve arrangement associated with the at least one aperture, the valve arrangement being secured to the graft about the at least one aperture; and, an outer liner connected to the tubular graft between the proximal end and the distal end and surrounding the valve arrangement. In some embodiments, the valve arrangement comprises a third biocompatible material having four sides, wherein three of the four sides are secured to the graft.

16 Claims, 9 Drawing Sheets

(52) U.S. Cl.
CPC ... *A61F 2002/072* (2013.01); *A61F 2002/077* (2013.01); *A61F 2250/0003* (2013.01)

(56) References Cited

U.S. PATENT DOCUMENTS

| | | |
|---|---|---|
| 8,167,926 B2 | 5/2012 | Hartley et al. |
| 8,474,120 B2 | 7/2013 | Hagaman et al. |
| 8,480,726 B2 | 7/2013 | Cunningham et al. |
| 8,556,960 B2 | 10/2013 | Agnew et al. |
| 8,636,789 B2 | 1/2014 | Ivancev et al. |
| 8,845,714 B2 | 9/2014 | Dimatteo et al. |
| 2005/0222674 A1 | 10/2005 | Paine |
| 2006/0161248 A1 | 7/2006 | Case et al. |
| 2007/0250154 A1 | 10/2007 | Greenberg et al. |
| 2008/0114446 A1* | 5/2008 | Hartley ............ A61F 2/07 623/1.13 |
| 2008/0188923 A1 | 8/2008 | Chu |
| 2010/0312326 A1 | 12/2010 | Chuter et al. |
| 2011/0022153 A1* | 1/2011 | Schreck ............ A61F 2/07 623/1.13 |
| 2011/0257725 A1* | 10/2011 | Argentine ........ A61F 2/07 623/1.15 |
| 2012/0053676 A1 | 3/2012 | Ku et al. |
| 2012/0203264 A1 | 8/2012 | Karwa et al. |
| 2012/0290069 A1* | 11/2012 | Ivancev ............ A61F 2/07 623/1.13 |
| 2013/0304196 A1 | 11/2013 | Kelly |
| 2014/0180393 A1 | 6/2014 | Roeder |
| 2014/0257453 A1 | 9/2014 | Roeder |
| 2014/0358221 A1 | 12/2014 | Ho et al. |

OTHER PUBLICATIONS

Jackson et al., Devices used for endovascular aneurysm repair: past, present, and future, NCBI, Seminars in Interventional Radiology, 2009, vol. 26, No. 1, pp. 39-43.
Schlosser et al., Pitfalls and complications of fenestrated and branched endografts, Endovascular Today, Feb. 2008, pp. 56-61.
European Search Report for Application No. 17275195.0 dated May 9, 2018.

* cited by examiner

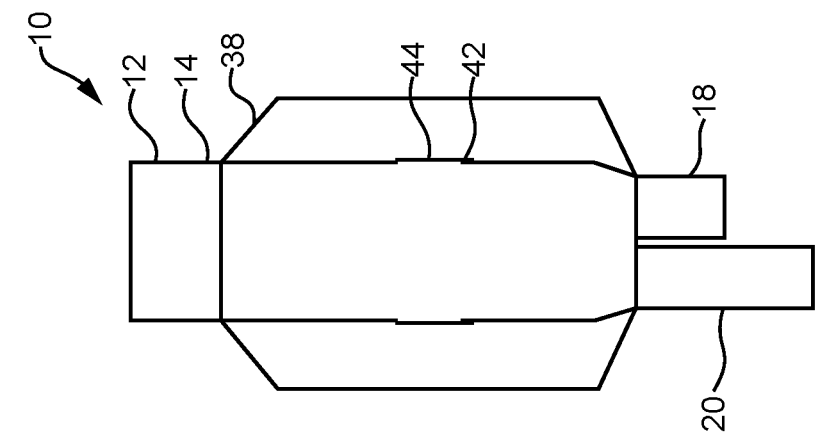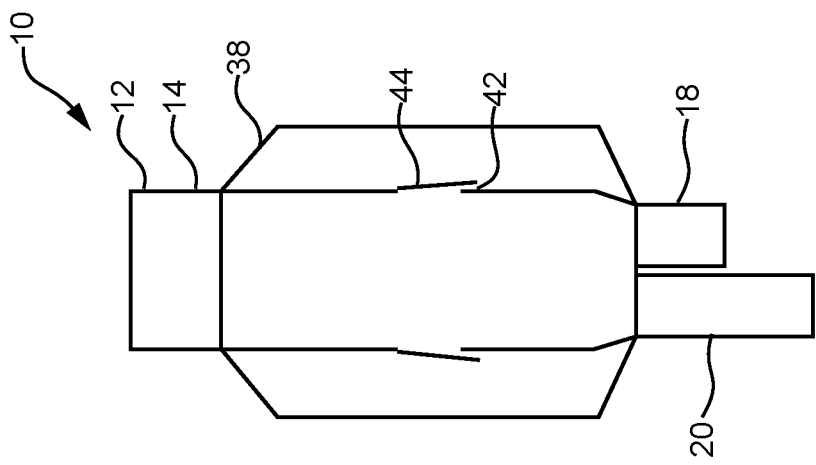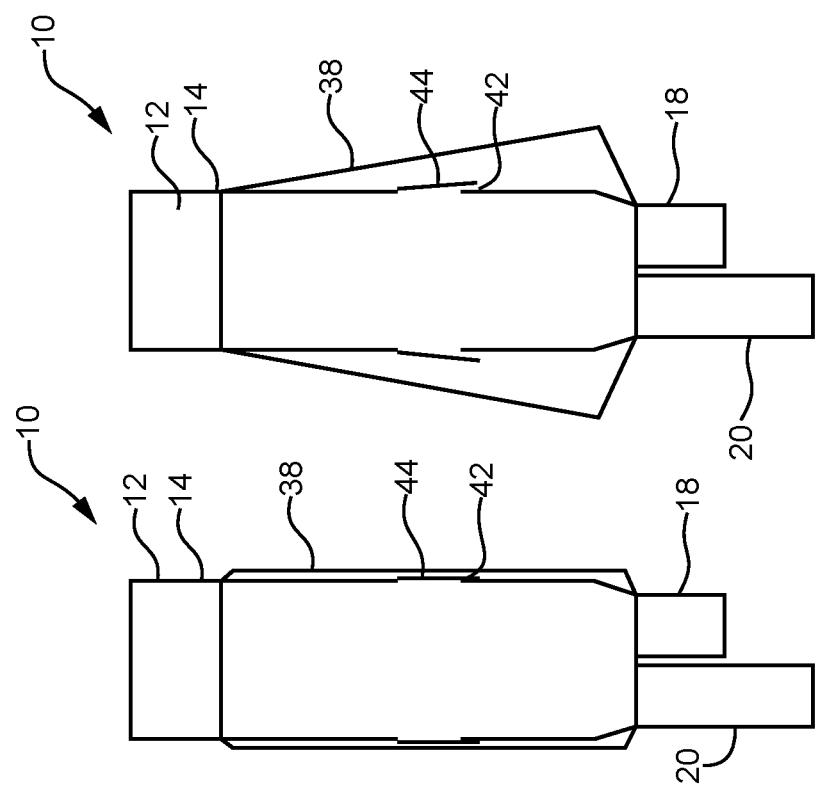

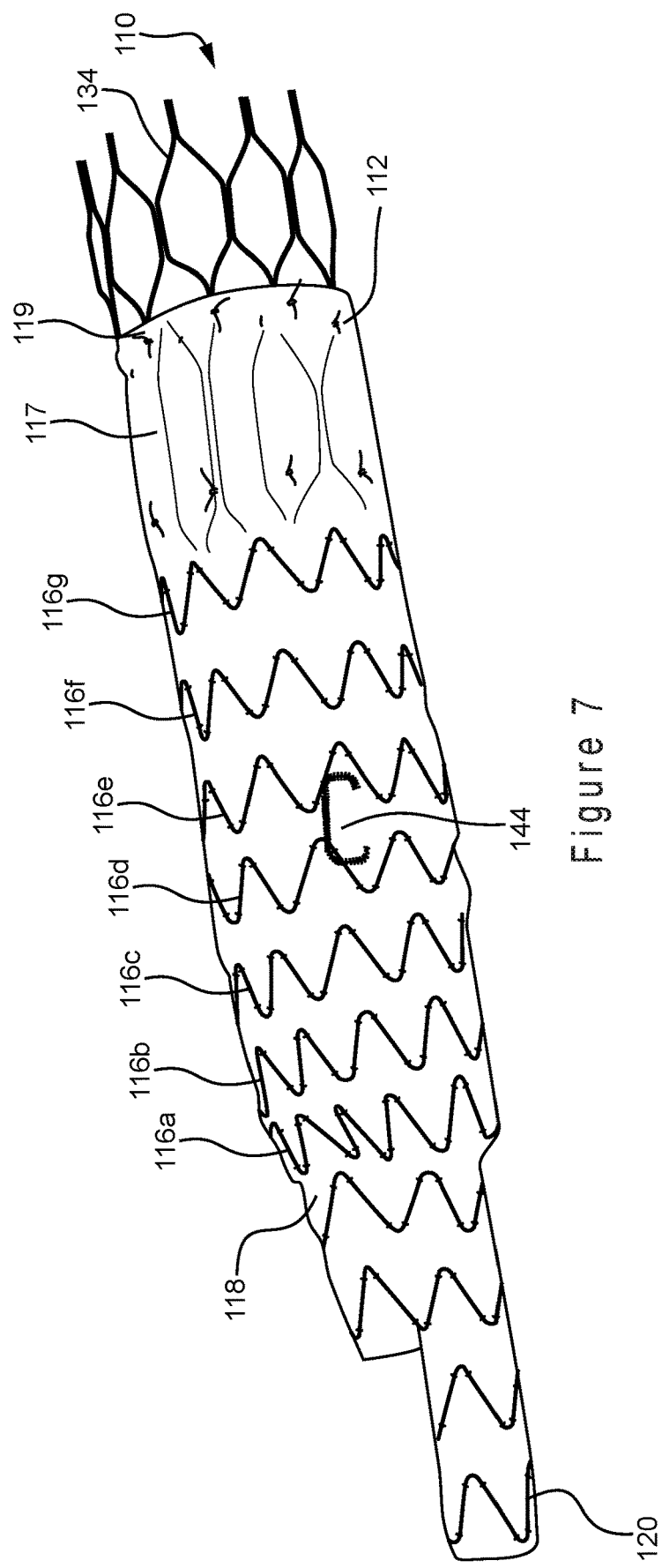

LOW PROFILE STENT GRAFT HAVING A CHECK VALVE

The present application claims priority to U.S. Provisional Patent Application Ser. No. 62/439,586 filed Dec. 28, 2016, the entirety of which is hereby incorporated by reference.

BACKGROUND

This invention relates generally to an endoluminal prosthesis and particularly to a endoluminal prosthesis having a valve arrangement that is implantable within the human or animal body for the repair of damaged vessels, ducts or other physiological passageways and cavities, and systems and methods for facilitating deployment of such an endoluminal prosthesis.

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or to preserve any remaining vascular integrity by replacing a length of the existing passageway or duct wall that spans the site of failure or defect. Endoluminal prostheses may be of a unitary construction or may be comprised of multiple prosthetic modules.

A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Upon placement of an endoluminal prostheses, in some cases, a endoleak may be present. Endoleaks are characterized by persistent blood flow within the aneurysm sac following endovascular aneurysm repair. A Type I endoleak is a leak that occurs near the top or bottom of the stent graft and may be caused as a result of an inadequate seal at the site of the endoluminal prosthesis attachment. A Type II endoleak, the most common type of endoleak, is a leak that occurs when retrograde flow through branch vessels that has been excluded via stent graft placement continue to fill the aneurysm sac. Common vessels for this retrograde flow are lumbar arteries, inferior mesenteric artery or internal iliac artery. A small fraction of these resolve without additional treatment, but reintervention is a common solution at significant risk to the patient. A Type III endoleak may be caused by a mechanical failure of the endoluminal prosthesis. A Type IV endoleak occurs when blood leaks across the graft due to porosity. If left untreated, there is a possibility that the aneurysm may expand and may create a greater risk of rupture.

BRIEF SUMMARY

Endoluminal prostheses and preforms of medical devices are described which may allow for increased flexibility while maintaining the integrity of an inner lumen thereof in tortuous anatomy. The invention may include any of the following aspects in various combinations, and may also include any other aspect described below in the written description or in the attached drawings.

In one aspect, an endoluminal prosthesis is provided including a graft having a tubular body and a surface comprising a first biocompatible material, the graft comprising a main lumen disposed therein, a proximal end, and a distal end, and an intermediate section positioned between the proximal end and the distal end; at least one aperture through a side wall of the intermediate section of the graft, the aperture in fluid communication with the main lumen; a valve arrangement connected to the intermediate section and associated with the at least one aperture, the valve arrangement having an open position and a closed position, and a liner comprising a second biocompatible material secured about the intermediate section and surrounding the valve arrangement. In some embodiments, the second biocompatible material has greater pliability than the second biocompatible material. In other embodiments, the aperture comprises a generally circular configuration or a slit configuration. In further embodiments, the endoluminal prosthesis further includes comprising a plurality of stents attached to the graft about the surface of the graft and arranged in longitudinally spaced rows, the stents comprising a plurality of struts interconnected by apices, wherein at least one of the plurality of stents is in an out-of-phase configuration. The valve arrangement may is positioned between the at least one stent in the out-of-phase configuration and an adjacent stent row.

In another aspect, an endoluminal prosthesis is provided including an tubular graft having a proximal end, a distal end, and a main lumen disposed therein, the tubular graft comprising a first biocompatible material; a plurality of stents disposed about a surface of the tubular graft and arranged in longitudinally spaced rows; at least one aperture disposed through a sidewall of the tubular graft, the at least one aperture positioned between two longitudinally spaced rows of stents; a valve arrangement associated with the at least one aperture, the valve arrangement being secured to the graft about the at least one aperture; and, an outer liner connected to the tubular graft between the proximal end and the distal end and surrounding the valve arrangement. In some embodiments, the valve arrangement comprises a third biocompatible material having four sides, wherein three of the four sides are secured to the graft. In other embodiments, the valve arrangement comprises a third biocompatible material having four sides and four corners, wherein the four corners are secured across struts on longitudinally adjacent rows of stents.

In yet another embodiment, an endoluminal prosthesis is provided including a bifurcated graft having a tubular body and a surface comprising a first biocompatible material, the graft comprising a main lumen disposed therein, a proximal end, and a distal end, and an intermediate section positioned between the proximal end and the distal end; a plurality of stents disposed about a surface of the tubular graft and arranged in longitudinally spaced rows, at least one of the plurality of stents having an out-of-phase configuration; at least one aperture through a side wall of the intermediate section of the graft, the aperture in fluid communication with the main lumen; a valve arrangement associated with the at least one aperture and connected to the intermediate section between the at least one stent row in the out-of-phase configuration and an adjacent stent row and, the valve arrangement having an open position and a closed position, and an outer liner comprising a second biocompatible material secured about the intermediate section and surrounding the valve arrangement.

BRIEF DESCRIPTION OF THE DRAWINGS

FIGS. 6A-6D illustrate the stages of the endoluminal prosthesis of FIG. 1 from a collapsed position to an expanded position.

FIG. 7 illustrates an alternative embodiment of an endoluminal device where an outer liner has been removed to show a valve arrangement.

DETAILED DESCRIPTION OF THE DRAWINGS AND THE PRESENTLY PREFERRED EMBODIMENTS

Figure 1:
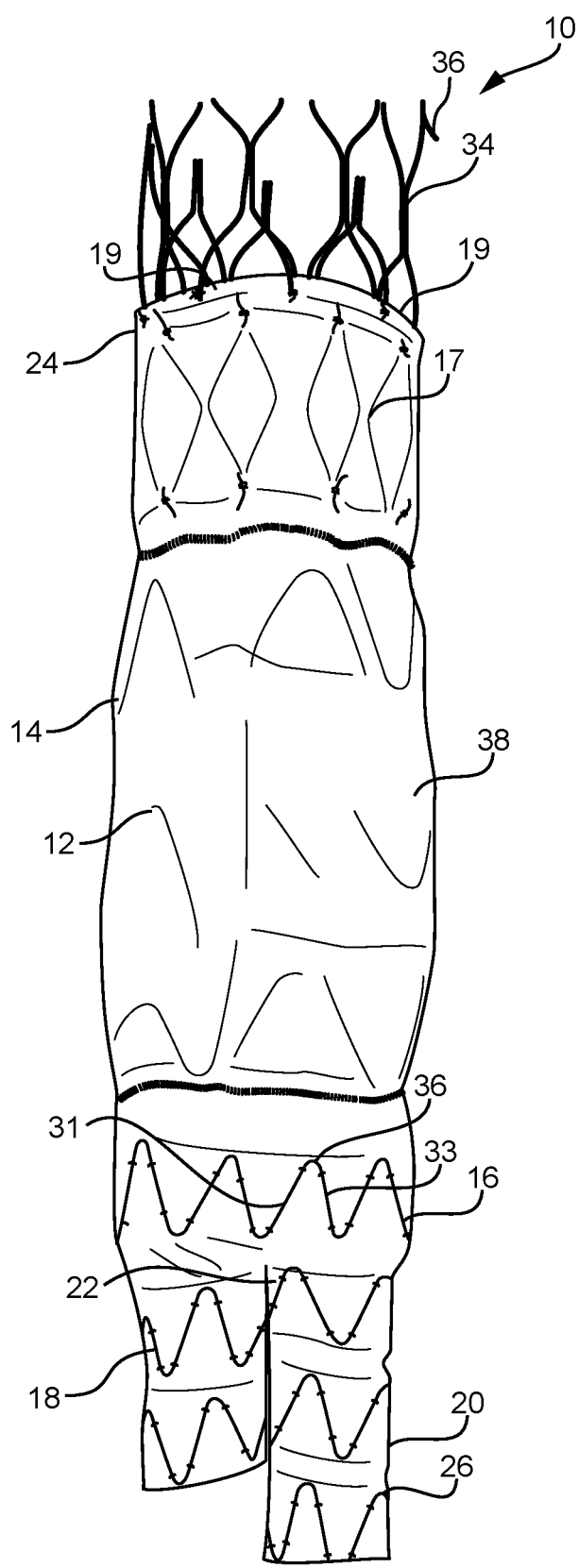
FIG. 1 illustrates an embodiment of an endoluminal device having a valve arrangement and an outer liner in a compressed position.

Unless defined otherwise, all technical and scientific terms used herein have the same meaning as commonly understood by one of ordinary skill in the art to which this invention pertains.

The term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the prosthesis delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first, and the outflow end (that end from which the fluid exits). When applied to other vessels similar terms such as caudal and cranial should be understood.

The term "aperture" means an opening provided through a surface of a prosthesis from the interior of the prosthesis to the exterior of the prostheses and may have a variety of geometries, including circular, semi-circular, oval, oblong, as well as other geometries.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents 16 may be comprised of a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as nitinol, or other suitable materials as known in the art. The stents may be made of a wire, or may be laser or cannula cut, or manufactured by other known methods.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a cross linked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPont. Dacron™ is known to be sufficiently biologically inert, non-biodegradable, and durable to permit safe insertion inside the human body.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

The terms "patient," "subject," and "recipient" as used in this application refer to any animal, especially humans.

The term "systole" refers to the phase of the heartbeat when the heart muscle contracts and pumps blood from the chambers into the arteries.

The term "diastole" refers to the phase of the heartbeat when the heart muscle relaxes and allows the chambers to fill with blood.

FIG. 1 illustrates an embodiment of an endoluminal prosthesis 10. The endoluminal prosthesis 10 includes a bifurcated graft 12 and may be placed within a diseased vessel in a configuration in which the endoluminal prosthesis 10 is substantially straight. The bifurcated graft 12 comprises a main body 14 having a generally tubular configuration defining a lumen disposed within and extending the length of the graft 12 associated with one or more stents 16. The main tubular body 14 includes a proximal end 15 and a lumen 19 extending through the prosthesis 10 to permit passage of blood flow through the prosthesis 10. The tubular graft material may be constructed from a biocompatible material. The bifurcated stent graft 12 has a short leg 18 and a long leg 20 extending from a bifurcation 22. The stents 16 may be placed on the external surface and/or internal surface of the graft material. In one particular embodiment, the prosthesis 10, such as that shown in FIG. 1, has external body stents 16 and an internal body stent 17. The internal stent 17 may be a sealing stent and placed at or near the proximal end 15 of the prosthesis 10 to seal the prosthesis 10 at the proximal end 15 to the walls of a blood vessel into which it has been placed. Additionally, or alternatively, depending on the location of the place of the prosthesis 10 or a particular need, a sealing stent 17 may be placed at either or both the proximal and distal ends 24, 26 of prosthesis 10. One example of a bifurcated stent graft includes the Zenith LP stent graft available from COOK, INC. (Bloomington, Ind.). In this embodiment, the stent graft 12 has a proximally extending supra-renal exposed stent 34 with barbs 36 engaging the wall of the aorta proximal of the renal arteries to provide a secure position to prevent migration of the stent graft. The prosthesis 10 also may include an attachment mechanism, for example, a proximally extending supra-renal exposed stent 34 with barbs 36, to further secure the prosthesis 10 within the body vessel and prevent migration of the prosthesis 10.

Stents 16, for example those shown in the Figures may be, for example zig zag stents, also known has Z-stents, that comprise a series of struts 31, 33 connected by apices 36, although the type of stent used is not so limited. The stents 16 may be either self-expanding or balloon expandable. Preferably, they are self-expanding. However, a combination of self-expanding and balloon expandable stents also may be contemplated.

As set forth above, the stents 16 include struts 31, 33 that are spaced apart from each other. The strut spacing is measured from bend-to-bend (or apex to apex 36). Stent amplitude, spacing and stagger are preferably optimized for each prosthesis design. In some aspects, the apices or bends 36 of the struts 31, 33 may be staggered for minimal contact with each other.

The prosthesis 10 further includes an outer liner 38 disposed about the main body 14 of the tubular graft 12. The outer liner 38 is comprised of a second biocompatible material. In one embodiment, the outer liner 38 may be comprised of the same biocompatible material as the tubular graft 12. In other embodiments, the second biocompatible material may be different that the biocompatible material of the tubular graft 12. For example, the second biocompatible material may have greater pliability than the first biocompatible graft material used for the tubular graft 12. In this embodiment, the outer liner 38 is secured to the main body graft. In one particular embodiment, the outer liner 38 may be secured to the main body graft distal to the internal sealing stent 17 and proximal to bifurcation 22. The outer liner 38 may have a generally tubular shape and be disposed circumferentially around the main body 14 of the tubular graft. The outer liner 38 has a diameter greater than the diameter of the main body graft. Accordingly, a space between the main body of the graft and the outer liner is sealed. As will be discussed below, the sealed space is configured to receive blood flowing from the lumen of the tubular graft through an aperture (not shown) and a valve arrangement (not shown) associated with the aperture. Thus, the outer liner 38 has a compressed configuration and an expanded configuration.

Figure 2:
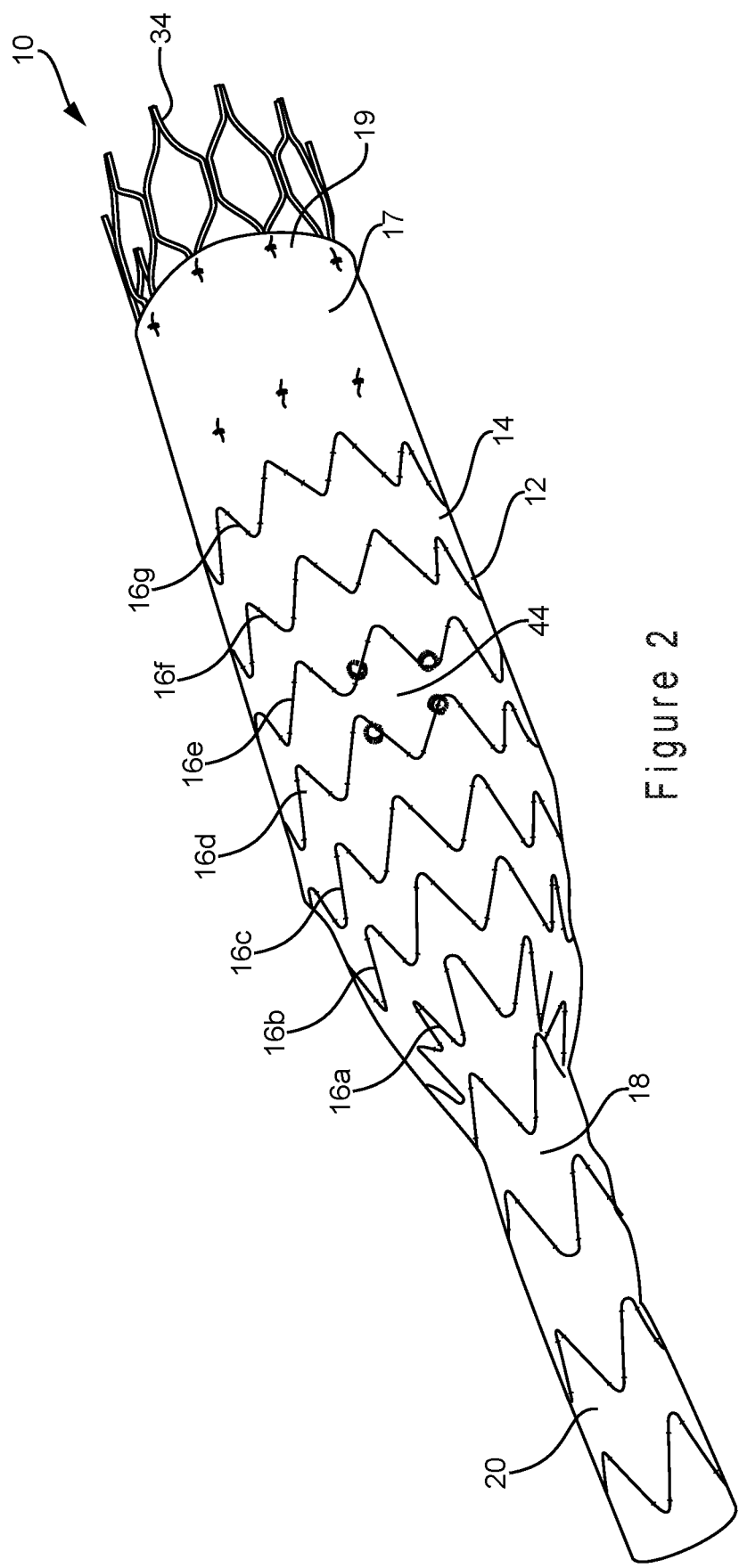
FIG. 2 illustrates the endoluminal device of FIG. 1, where the outer liner has been removed to show a valve arrangement.

FIG. 2 shows the prosthesis 10 with the outer liner removed. The endoluminal prosthesis 10 includes a bifurcated graft 12 and may be placed within a diseased vessel in a configuration in which the endoluminal prosthesis 10 is substantially straight. The bifurcated graft 12 comprises a main body 14 having a generally tubular configuration defining a lumen disposed within and extending the length of the graft 12 associated with one or more stents 16. The main tubular body 14 includes a proximal end 15 and a lumen 19 extending through the prosthesis 10 to permit passage of blood flow through the prosthesis 10. The bifurcated stent graft 12 has a short leg 18 and a long leg 20 extending from a bifurcation 22. In one particular embodiment, the main body 12 of the prosthesis 10, such as that shown in FIG. 2, has external body stents 16a-g and an internal body stent 17. The stents 16a, 16b, 16c, 16f, and 16g are positioned longitudinally adjacent to each other and the apices of each row are in circumferential alignment, or "in phase", with the apices of longitudinally adjacent rows. Likewise, 16f and 16g are positioned longitudinally adjacent to each other and the apices are in phase. As shown in FIG. 2, the stent 16d is positioned "out of phase" by about 180 degrees with longitudinally adjacent row 16e, such that circumferentially about the surface of the graft, every other apex of the internal stent 16d matches with every other apex of stent row 16e. The distance between matching apices may range from 1 mm to 4 mm. In one embodiment, the spacing may be 2 mm. In other embodiments, the stent 16d may be positioned in phase with longitudinally adjacent row 16e, or the internal stent 16d may be out of phase by an amount less than 180 degrees. Positioned between external stents 16d and 16e is an embodiment of a valve arrangement 44 for an aperture (not shown) disposed through a side wall of the main body 14 of the graft 12. The prosthesis 10 also may include a proximally extending supra-renal exposed stent 34 with barbs 36, to further secure the prosthesis 10 within the body vessel.

Figure 3:
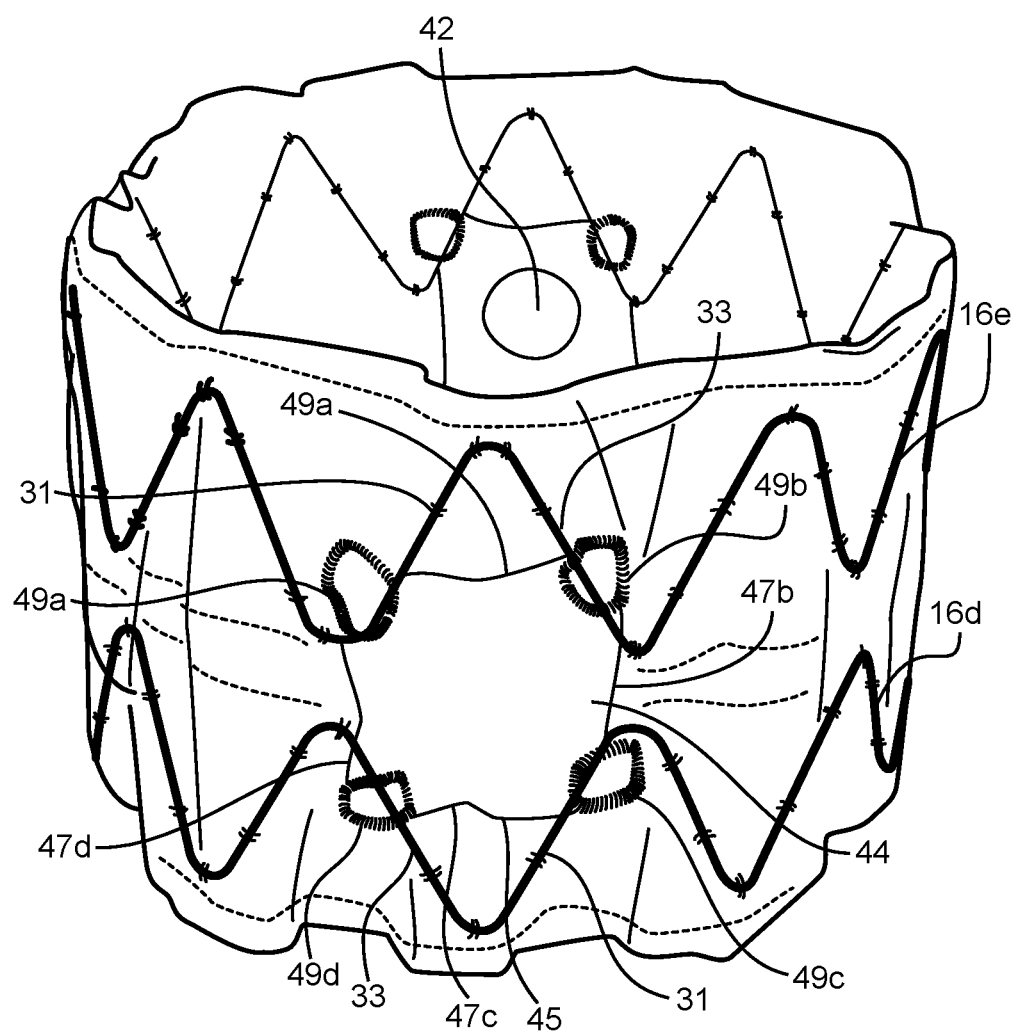
FIG. 3 is a profile view of the aperture 42 and the valve arrangement 44 of the endoluminal device of FIG. 1.

FIG. 3 provides profile view of the aperture 42 and the valve arrangement 44. In this embodiment, the graft includes two openings or apertures 42 that extend from an internal surface to the external surface 22 of the graft 12. As shown, the apertures 42 have a generally circular configuration and allow for fluid communication between the outer liner 38 and the lumen of the graft 12. The apertures 42 are configured to be sufficiently large enough to allow the flow of blood 12 to the space between outer liner 38 and the external surface of the graft 12. The apertures 42 may range in size from 0.1 mm to 6 mm. The valve arrangement 44 comprises a third biocompatible material 45 having a generally quadrangular shape with four sides 47a-47d and four corners 49a-49d. The third biocompatible material 45 of the valve arrangement 44 is secured to the main body of the graft about the aperture 42 at the corners 49a-49d of the valve arrangement 44. In a particular embodiment, portions of the third biocompatible material 45 of the valve arrangement may extend over struts 32, 34 of adjacent stent rows 16e and 16f. As shown in this embodiment, corner 49a, formed by sides 47a and 47d, and corner 49b, formed by sides 47a and 47b, are positioned over adjacent struts 31, 33 of stent 16e. Likewise, corners 49c, formed by sides 47b and 47c, and 49d, formed by sides 47c and 47d, are positioned over adjacent struts 31, 33 of stent 16d. In one particular embodiment, the securing mechanism is a suture material. However, other securing mechanisms, including but not limited to, adhesives and other bonding materials may be used.

The unsecured sections of the sides 47a-47d provide openings 46 between the third biocompatible material 145 of the valve arrangement 144 and the graft 12. The valve arrangement 44 allows blood to flow from the lumen of the graft 12 to the space between outer liner 38 and the external surface of the graft 12. The valve arrangement 44 is configured to allow for the flow of blood through the openings 46 due to the differences of pressure within the internal lumen and the aneurysmal sac. One of skill understands that upon placement of the prosthesis 10 within the aorta of the patient, the pressure within the aorta, and in turn, the prosthesis, would be greater than the pressure within the aneurysmal sac, as blood flows through the prosthesis and not through the aneurysmal sac. Upon filling the space between the outer liner 38 and the graft 12, any retrograde flow closes the valve and prevents blood from flowing from that space back into the interior lumen.

Figure 4A:
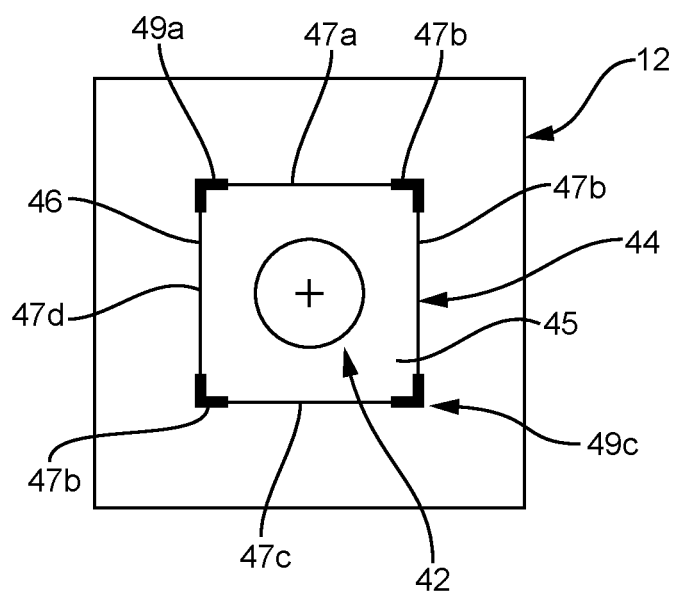
FIGS. 4A and 4B illustrate a schematic view of this embodiment of the aperture and the valve arrangement.
Figure 4B:
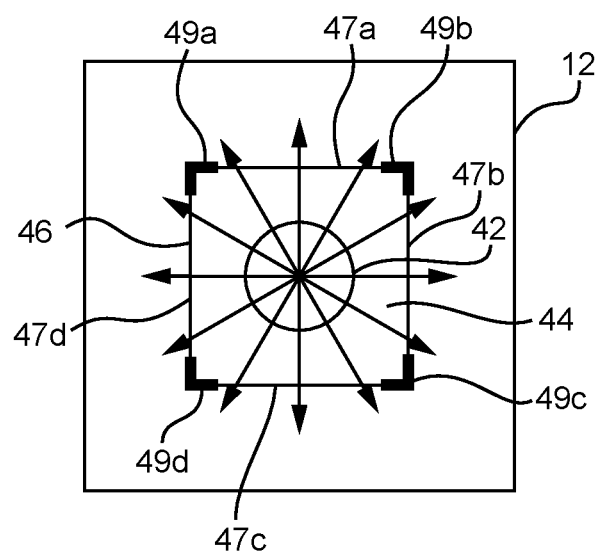

FIGS. 4A and 4B show a schematic view of this embodiment of the aperture and the valve arrangement. As shown, the main graft 12 includes a generally circular aperture 42. Surrounding the aperture 42 is the valve arrangement 44. As discussed above, the valve arrangement 44 is secured to the main body of the graft 12 about the aperture 42 at the corners 49a-49d of the third biocompatible material 45 of the valve arrangement 44. Between each securement point of the valve arrangement to the main graft body are openings 46 formed from the unsecured portions of the sides 47a-47d of the third compatible material 45 of the valve arrangement 44, which allow fluid communication to the open space. The openings 46 of the valve arrangement 44 allows for flow paths from the aperture 42 to the space in substantially all directions about the circumference of the aperture 42, as shown in FIG. 4B and represented by the arrows.

Figure 5:
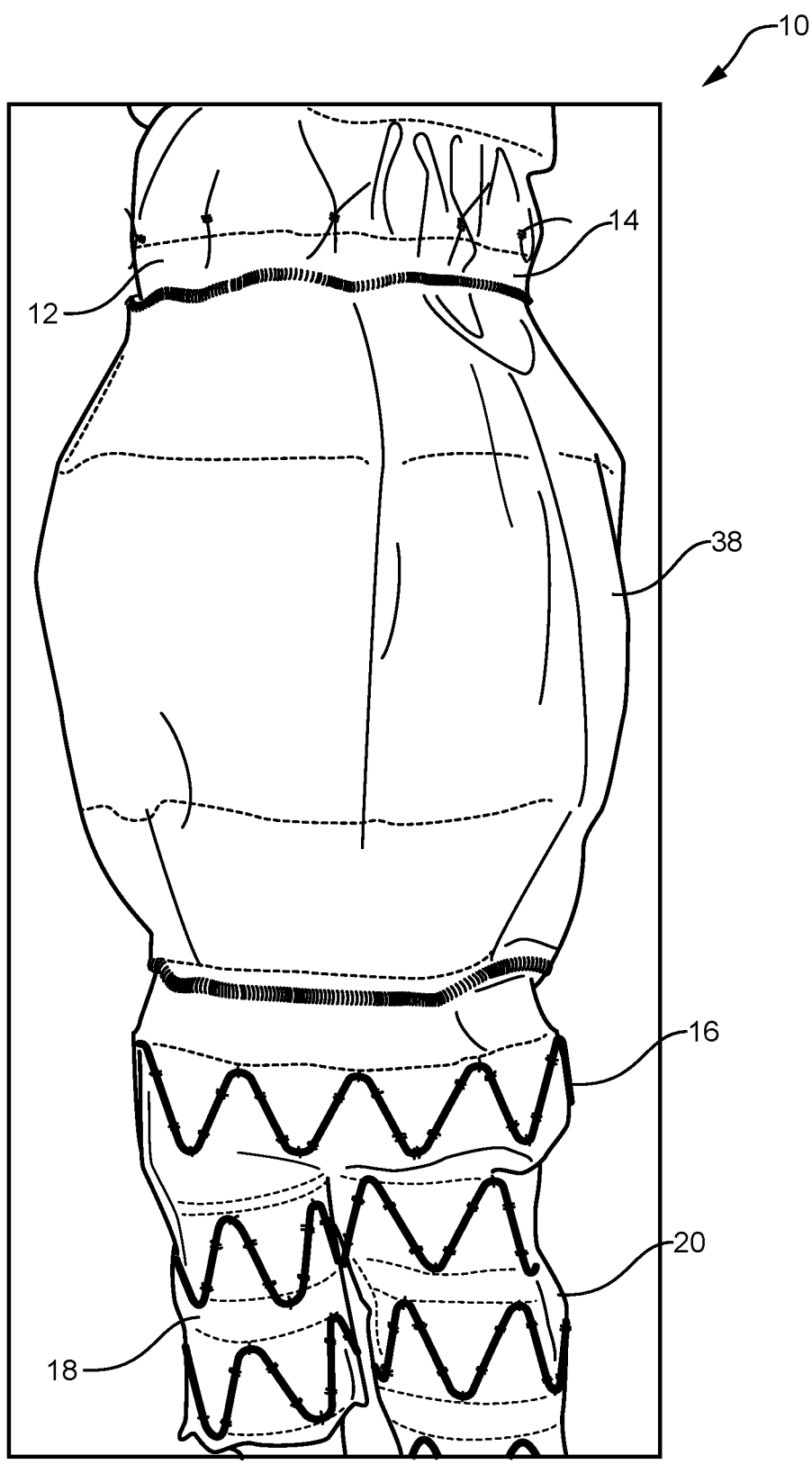
FIG. 5 illustrates the endoluminal prosthesis of FIG. 1 in an expanded position.

FIG. 5 illustrates the endoluminal prosthesis 10 where the outer liner 38 is in an expanded configuration. As discussed above, the valve arrangement allows for blood to flow from the lumen 19 of the graft 12 into the sealed space within the outer liner 38 and cause the outer liner to move from a configured position to an expanded configuration. As such, the filling of the space and equilibration of the pressure within the space helps to eliminate a Type II endoleak because the aortic pressure exceeds the pressure of the vessels communicating with the aneurysm sac. In some embodiments, the outer liner 38 may be configured to expand such that it fills substantially all of the volume of the aneurysm sac. In other embodiments, the outer liner 38 may be configured to expand such that it partially fills the volume of the aneurysm sac. Additionally, the outer liner 38 may occlude lumbar arteries, inferior mesenteric artery or internal iliac artery, which one of skill understands may be subject to retrograde flow once the graft is placed within the aorta and blood flows from the aorta is prevented from flowing into the aneurysm. Advantageously, the endoluminal prosthesis 10 allows for treatment of an endoleak, such as a Type II endoleak, without the need for reintervention into the patient of additional medical materials. Thus, the endoluminal prosthesis 10 reduces the risk to the patient during the procedure.

FIGS. 6A-6D illustrates the stages of the endoluminal prosthesis 10 when in use. Referring to FIG. 6A, the outer liner surrounding the main body 14 of the tubular graft 12 is in a compressed position. The tubular graft will generally be in this position upon deployment within the vessel of the patient. Once deployed within the vessel of the patient, blood will flow through the lumen 18 of the tubular graft 12 as the aortic pressure rises. When the pressure within the prosthesis 10 increases, the valve arrangement 44 will move from a closed position to an open position, which will allow blood to flow from the lumen through the aperture 42 and into the space between the exterior surface of the tubular graft 12 and the outer liner 38. Referring to FIG. 6B, the outer liner 38 is in a partially expanded configuration. As the volume between the outer liner 38 and the aneurysmal aortic wall is eliminated due to filling of the space between the outer liner 38 and the external surface of the main body 14 of the tubular graft 12, the pressure between the lumen of the graft and the space begins to equalize. FIGS. 6C and 6D shows the prosthesis when the space is fully inflated during systole and diastole, respectively. During systole, while the valve is in an open position, as shown in FIG. 6C, the pressure between the outer liner 38 and the stent graft 12 has equalized and the flow of blood from the lumen to the space is minimized. During diastole, as shown in FIG. 6D, the retrograde flow closes the valve, effectively sealing the aperture, and the flow of blood from the interior lumen into the space is prevented. Once the outer liner 38 has been fully expanded, the valves may become permanently occluded due to development of clot as intended. Patient blood stagnating in the space between the liner and the graft may also begin to clot, which may result in the liner becoming filled with a clot.

FIG. 7 shows an alternative embodiment of a prosthesis 110. As shown, the outer liner has been removed. The endoluminal prosthesis 110 includes a bifurcated graft 112 and may be placed within a diseased vessel in a configuration in which the endoluminal prosthesis 110 is substantially straight. The bifurcated graft 112 comprises a main body 114 having a generally tubular configuration defining a lumen disposed within and extending the length of the graft 112 associated with one or more stents 116. The main tubular body 114 includes a proximal end 115 and a lumen 119 extending through the prosthesis 110 to permit passage of blood flow through the prosthesis 110. The bifurcated stent graft 112 has a short leg 118 and a long leg 120 extending from a bifurcation 122. The stents 116 may be placed on the external surface 124 and/or internal surface 126 of the graft material. In one particular embodiment, the prosthesis 110, such as that shown in FIG. 7, has external body stents 116a-f and an internal body stent 117. The stents 116a, 116b, 116c are positioned longitudinally adjacent to each other and the apices of each row are in circumferential alignment, or "in phase", with the apices of longitudinally adjacent rows. As shown in FIG. 7, the stent 116d is positioned "out of phase" by about 180 degrees with longitudinally adjacent row 116e, such that circumferentially about the surface of the graft, every other apex of the internal stent 116d matches with every other apex of stent row 116e. The distance between matching apices may range from 1 mm to 4 mm. In one embodiment, the spacing may be 2 mm. In other embodiments, the internal stent 116d may be positioned in phase with longitudinally adjacent row 116e, or the internal stent 116d may be out of phase by an amount less than 180 degrees. Positioned between external stents 116d and 116e is an embodiment of a valve arrangement 145 for a aperture (not shown) disposed through a side wall of the main body 114 of the graft 112. In this embodiment, the stent graft 112 has a proximally extending supra-renal exposed stent 134 with barbs 136 engaging the wall of the aorta proximal of the renal arteries to provide a secure position to prevent migration of the stent graft. The prosthesis 110 also may include an attachment mechanism, for example, a proximally extending supra-renal exposed stent 134 with barbs 136, to further secure the prosthesis 110 within the body vessel and prevent migration of the prosthesis 110.

Figure 8:
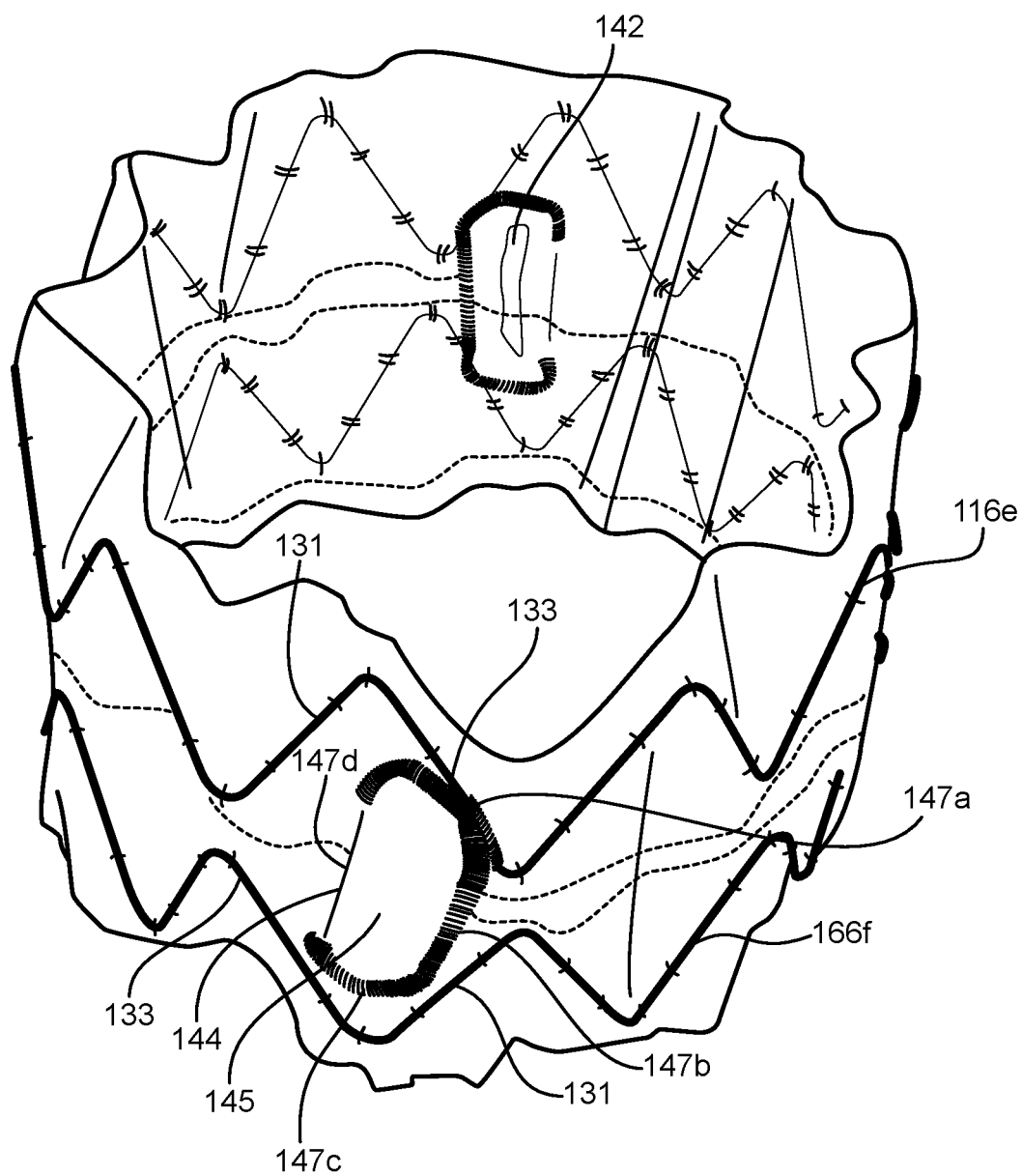
FIG. 8 is a profile view of a aperture and a valve arrangement of the endoluminal device of FIG. 6.

FIG. 8 provides profile view of the aperture and the valve arrangement. In this embodiment, the graft includes two openings or apertures 142 that extend from an internal surface to the external surface 122 of the graft 112. As shown, the apertures 142 comprise a narrow slit in the longitudinal direction and are configured to allow for fluid communication between the outer liner and the lumen of the graft 112. The apertures 142 are configured to be sufficiently large enough to allow the flow of blood 12 to the space between outer liner and the external surface of the graft 112.

In this embodiment, the apertures 142 are generally sized less than or equal to 1 mm. The valve arrangement 144 comprises a third biocompatible material 145 having a generally quadrangular shape with four sides 147a-147d and four corners 149a-149d. The third biocompatible material 145 of the valve arrangement 144 is secured to the main body of the graft 112 about the aperture 142 on three sides 147a, 147b, and 147c of the third biocompatible material 145 of the valve arrangement 144. As shown, sides 147a and 147b are cross over adjacent struts 131, 133 of stent 16e. Likewise, sides 147b and 147c are positioned over adjacent struts 31, 32 of stent 16d. The securing mechanism secures the third biocompatible material 145 to the main body of the graft 112 and at least partially adjacent to the struts 31, 33 of stents 116d and 116e. In one particular embodiment, the securing mechanism is a suture material. However, other securing mechanisms, including but not limited to, adhesives and other bonding materials may be used.

Side 147d of the third biocompatible material 145 of the valve arrangement 144 remains unsecured provides an opening 146. The valve arrangement 144 allows for blood to flow from the lumen of the graft 112 to the space between the outer liner and the external surface of the graft 112 through the aperture 142. The valve arrangement 144 is configured to allow for the flow of blood through the opening 146 due to the differences of pressure within the internal lumen 119 and the aneurysmal sac. One of skill understands that upon placement of the prosthesis 110 within the aorta of the patient, the pressure within the aorta, and in turn, the prosthesis 110, would be greater than the pressure within the aneurysmal sac, as blood flows through the prosthesis and not through the aneurysmal sac. Upon filling the space between the outer liner and the graft 112, any retrograde flow closes the valve and prevents blood from flowing from that space back into the interior lumen.

Figure 9A:
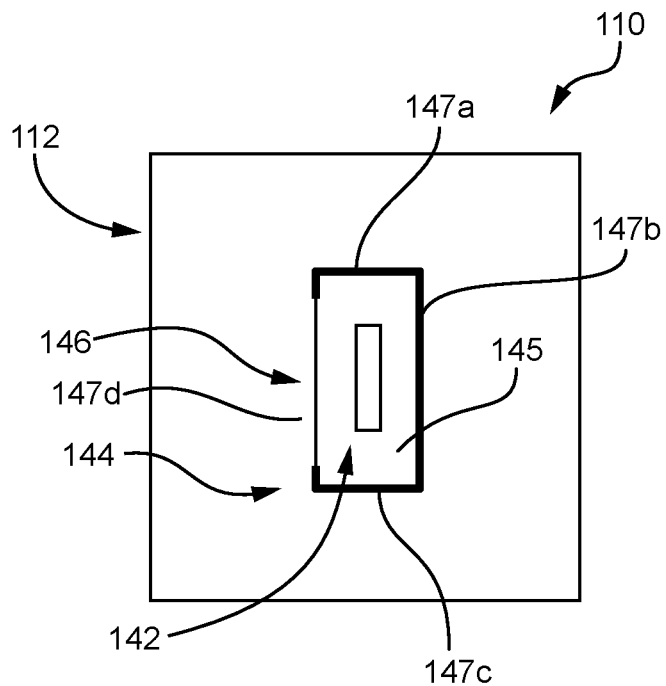
FIGS. 9A and 9B illustrate a schematic view of this embodiment of the aperture and the valve arrangement.
Figure 9B:
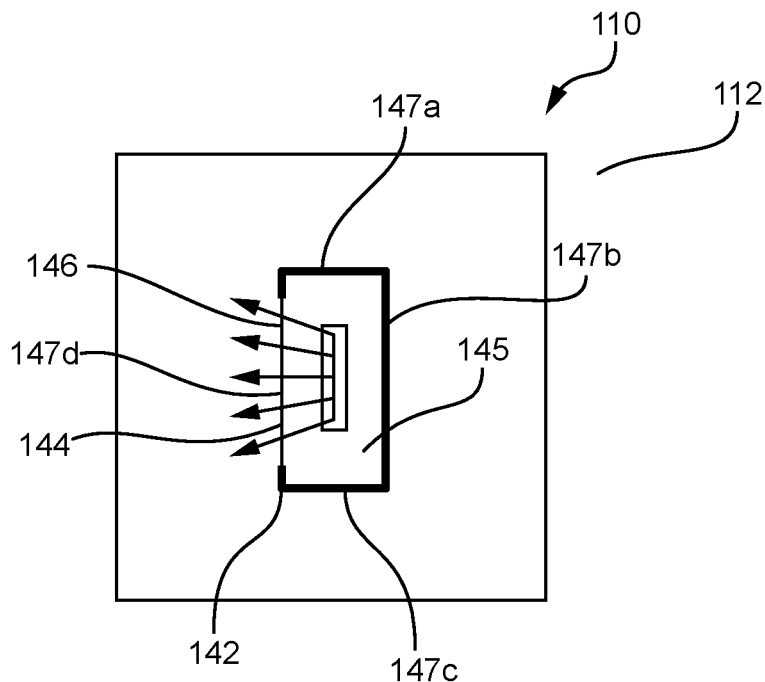

FIGS. 9A and 9B show a schematic view of this embodiment of the aperture and the valve arrangement. As shown, the main graft 112 includes a aperture 142 comprising a narrow slit in the longitudinal direction. Surrounding the aperture 142 is the valve arrangement 144. As discussed above, the third biocompatible material 145 of the valve arrangement 144 is secured to the main body of the graft 112 about the aperture 142 on three sides 147a, 147b, and 147c. Side 147d of the third biocompatible material 145 of the valve arrangement 144 remains unsecured provides an opening 146, which allows fluid communication to the open space. The opening 146 of the valve arrangement 144 allows for flow paths from the aperture to the space in the direction of the opening 146, as shown in FIG. 9B.

In use, the outer liner surrounding the main body 14 of the tubular graft 12 is in a compressed position. The tubular graft will generally be in this position upon deployment within the vessel of the patient. Once deployed within the vessel of the patient, blood will flow through the lumen 118 of the tubular graft 112 as the aortic pressure rises. When the pressure within the prosthesis 110 increases, the valve arrangement 144 will move from a closed position to an open position, which will allow blood to flow from the lumen through the aperture 142 and into the space between the exterior surface of the tubular graft 112 and the outer liner. As the volume between the outer liner 38 and the aneurysmal aortic wall is eliminated due to filling of the space between the outer liner and the external surface of the main body 14 of the tubular graft 12, the pressure between the lumen of the graft and the space begins to equalize. As such, the filling of the space and equilibration of the pressure within the space helps to eliminate a Type II endoleak because the aortic pressure exceeds the pressure of the vessels communicating with the aneurysm sac. Once the space is filled, during systole, the pressure between the outer liner 38 and the stent graft 12 has equalized and the flow of blood from the lumen to the space is minimized. Retrograde flow closes the valve, effectively sealing the aperture, and the flow of blood from the interior lumen into the space is prevented. Once the outer liner 38 has been fully expanded, the valves may become permanently occluded due to development of clot as intended. Patient blood stagnating in the space between the liner and the graft may also begin to clot, which may result in the liner becoming filled with a clot.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. An endoluminal prosthesis, comprising:
   a graft having a tubular body and a surface comprising a first biocompatible material, the graft comprising a main lumen disposed therein, a proximal end, and a distal end, and an intermediate section positioned between the proximal end and the distal end,
   a plurality of stents attached to the intermediate section of the graft about the surface and arranged in longitudinally spaced rows, the stents comprising a plurality of struts interconnected by apices;
   at least one aperture through a side wall of the intermediate section of the graft, the aperture in fluid communication with the main lumen;
   a valve arrangement connected to the intermediate section and associated with the at least one aperture, the valve arrangement having an open position and a closed position, and;
   a liner comprising a second biocompatible material secured about the intermediate section and surrounding the valve arrangement,
   wherein the valve arrangement is positioned between adjacent rows of stents, wherein at least one of the plurality of stents is in an out-of-phase configuration, and wherein the valve arrangement is positioned between the at least one of the plurality of stents in the out-of-phase configuration and an adjacent stent row.

2. The endoluminal prosthesis of claim 1, wherein the second biocompatible material has greater pliability than the first biocompatible material.

3. The endoluminal prosthesis of claim 1, wherein the aperture comprises a generally circular configuration.

4. The endoluminal prosthesis of claim 1, wherein the aperture comprises a slit in a longitudinal direction.

5. The endoluminal prosthesis of claim 1, wherein the valve arrangement comprises a third biocompatible material having four sides, wherein three of the four sides are secured to the graft.

6. The endoluminal prosthesis of claim 1, wherein at least one side of the valve arrangement is secured adjacent to struts on longitudinally adjacent rows of stents.

7. The endoluminal prosthesis of claim 1, wherein the valve arrangement comprises a third biocompatible material having four sides and four corners, wherein the four corners are secured across struts on longitudinally adjacent rows of stents.

8. The endoluminal prosthesis of claim 7, wherein the four sides of the valve arrangement remain unsecured.

9. An endoluminal prosthesis, comprising:
   a tubular graft having a proximal end, a distal end, an intermediate section positioned between the proximal end and the distal end, and a main lumen disposed therein, the tubular graft comprising a first biocompatible material;
   a plurality of stents disposed about a surface of the intermediate section of the tubular graft and arranged in longitudinally spaced rows;
   at least one aperture disposed through a sidewall of the tubular graft, the at least one aperture positioned between two longitudinally spaced rows of stents;
   a valve arrangement associated with the at least one aperture, the valve arrangement being secured to the tubular graft about the at least one aperture; and,
   an outer liner comprising a second biocompatible material and connected to the tubular graft between the proximal end and the distal end and surrounding the valve arrangement,
   wherein the valve arrangement is positioned between adjacent rows of stents, wherein at least one of the plurality of stents is in an out-of-phase configuration, and wherein the valve arrangement is positioned between the at least one of the plurality of stents in the out-of-phase configuration and an adjacent row of stents.

10. The endoluminal prosthesis of claim 9, wherein the second biocompatible material has greater pliability than the first biocompatible material.

11. The endoluminal prosthesis of claim 9, wherein the aperture comprises a generally circular configuration.

12. The endoluminal prosthesis of claim 9, wherein the aperture comprises a slit in a longitudinal direction.

13. The endoluminal prosthesis of claim 9, wherein the tubular graft further comprises a first leg and a second leg separated by a bifurcation, the first leg and the second leg extending from the distal end of the tubular graft.

14. The endoluminal prosthesis of claim 9, wherein the valve arrangement comprises a third biocompatible material having four sides, wherein three of the four sides are secured to the tubular graft.

15. The endoluminal prosthesis of claim 9, wherein the valve arrangement comprises a third biocompatible material having four sides and four corners, wherein the four corners are secured across struts on longitudinally adjacent rows of stents.

16. An endoluminal prosthesis, comprising:
   a bifurcated graft having a tubular body and a surface comprising a first biocompatible material, the bifurcated graft comprising a main lumen disposed therein, a proximal end, and a distal end, and an intermediate section positioned between the proximal end and the distal end;
   a plurality of stents disposed about a surface of the intermediate section of the bifurcated graft and arranged in longitudinally spaced rows, at least one of the plurality of stents having an out-of-phase configuration;
   at least one aperture through a side wall of the intermediate section of the bifurcated graft, the aperture in fluid communication with the main lumen;
   a valve arrangement associated with the at least one aperture and connected to the intermediate section between the at least one of the plurality of stents in the out-of-phase configuration and an adjacent stent row and, the valve arrangement having an open position and a closed position, and;

an outer liner comprising a second biocompatible material secured about the intermediate section and surrounding the valve arrangement.

\* \* \* \* \*